(12) United States Patent
Han et al.

(10) Patent No.: US 8,999,719 B2
(45) Date of Patent: Apr. 7, 2015

(54) QUALITY CONTROL MARKER AND ITS USE IN HERBS AUTHENTICATION

(71) Applicant: Hong Kong Baptist University, Kowloon (HK)

(72) Inventors: Quanbin Han, Kowloon (HK); Hubiao Chen, Kowloon (HK); Jun Xu, Kowloon (HK)

(73) Assignee: Hong Kong Baptist University, Kowloon (HK)

( * ) Notice: Subject to any disclaimer, the term of this patent is extended or adjusted under 35 U.S.C. 154(b) by 0 days.

(21) Appl. No.: 13/940,944

(22) Filed: Jul. 12, 2013

(65) Prior Publication Data

US 2015/0017734 A1     Jan. 15, 2015

(51) Int. Cl.
    *G01N 33/00* (2006.01)
(52) U.S. Cl.
    CPC ... *G01N 33/0098* (2013.01); *Y10T 436/143333* (2015.01); *Y10T 436/25375* (2015.01)
(58) Field of Classification Search
    CPC ............... G01N 33/0098; Y10T 436/143333; Y10T 436/25; Y10T 436/25375
    USPC ........ 436/94, 161, 174, 177, 178; 422/69, 70, 422/527, 533, 534; 210/635, 656, 198.2
    See application file for complete search history.

(56) References Cited

U.S. PATENT DOCUMENTS 8,354,127 B2 * 1/2013 Wong et al. .................. 424/725

OTHER PUBLICATIONS

Xu et al. Analytical and Bioanalytical Chemistry, vol. 406, Aug. 9, 2014, pp. 6409-6417.*
Zha et al. Journal of National Medicine, vol. 66, Jan. 20, 2012, pp. 525-534.*
Li et al. Chinese Medicine, vol. 3:7, Jun. 28, 2008, pp. 1-16.*
Xia et al. Journal of Functional Foods, vol. 4, Jan. 17, 2012, pp. 294-301.*

* cited by examiner

*Primary Examiner* — Maureen Wallenhorst
(74) *Attorney, Agent, or Firm* — Renner Kenner Greive Bobak Taylor & Weber

(57) ABSTRACT

The present invention relates to a quality control marker and method of using such marker in qualitative and quantitative authentication of *Dendrobium officinale* Kimura et Migo, which is known as a Chinese medicine under the name of *Tiepi Shihu* (鉄皮石斛).

17 Claims, 7 Drawing Sheets

QUALITY CONTROL MARKER AND ITS USE IN HERBS AUTHENTICATION

FIELD OF INVENTION

The present invention relates to a quality control marker and method of using such marker in qualitative and quantitative authentication of herbal materials, in particular but not limited to *Dendrobium* species. More particularly, the present invention relates to a chemical marker and its use in quick, efficient and low-cost authentication of *Dendrobium officinale* Kimura et Migo, which is well-known as an expensive Chinese medicine under the name of *Tiepi Shihu* (鉄皮石斛).

BACKGROUND OF INVENTION

Quality control of carbohydrates, especially polysaccharides and oligosaccharides, in herbal materials remains a challenge due to their complicated structures and macromolecular mass. Generally, isolation and purification followed by complete structural characterization, namely homogeneity and molecular weight determination, compositional monosaccharide analysis, glucosidic linkage type confirmation and then repetitive structural unit speculation, etc., is the most reliable method for quality evaluation of polysaccharides and oligosaccharides in herbal materials. As known in the art, however, the relevant methodologies are extremely intricate, difficult and time consuming and therefore not suitable for routine quality control method development. Besides, two kinds of analytical methods, total sugar content determination as well as sugar composition analysis, have been widely employing for quality control of carbohydrates in herbal materials. But the methods are still defective. Total sugar content determination by colorimetric method bears very poor specificity and is therefore inapplicable for qualitative purpose. And sugar composition analysis needs complicated operations, like acid hydrolysis, derivation, and followed by qualitative and quantitative determination of sugar derivatives using HPLC (high performance liquid chromatography) or GC (gas chromatography) (FIG. 1A). Hence, the experimental results are always affected by multiple factors in the tedious operating procedure, e.g. the temperature, reaction time and acid concentration of acid hydrolysis, and are therefore significantly variable. Furthermore, the method might be one-sided and could not reflect the original existence of polysaccharides and oligosaccharides before acid hydrolysis. Consequently, more convenience and reasonable method is imperative for quality control of carbohydrates in herbal materials.

*Dendrobium* is one of the largest genera in the plant family Orchidaceae. More than 1100 species of *Dendrobium* have been identified, with a wide distribution throughout Asia, Europe and Australia. The fresh or dried stems of about thirty *Dendrobium* species are collectively regarded as a famous tonic herb, namely *Shihu* in Chinese. Documented as a "superior grade" herb in "*Shennong Bencao Jing*", an ancient textbook on herbal materials in China, *Dendrobium* has been used for thousands of years for its traditional nourishing properties, such as benefiting stomachs, supplementing body fluids and strengthening immunity. Among them, *Dendrobii Officinalis Caulis*, called *Tiepi Shihu* in Chinese, which is derived from dried stems of *Dendrobium officinale* Kimura et Migo, is traditionally recognized as the best *Shihu* for tonic purpose, such as nourishing stomach, protecting throat and benefiting eyes. In "*Dao Zang*", a classic encyclopedia of Taoism, *Dendrobii Officinalis Caulis* was ever listed as the first one of "the Nine Herbs for Immortality of China". Nowadays, due to extremely scarce wild resource and distinguished tonic effects, it has been the most renowned and rarest *Dendrobium* herbs and has become one of the most expensive herbs in herbal markets worldwide, particularly in Southeast Asia. The stems of *D. officinale* are always heated and then twisted to a spiral or spring form followed by drying for sell in herbal markets and commonly known as *Tiepi Fengdou* (FIG. 2). The uncharacteristic appearance and high price of *Tiepi Fengdou* could lead to the occurrence of the adulterants, confused species, and counterfeits. Authentication and quality evaluation of *Tiepi Fengdou* is therefore crucial for ensuring the safety and efficacy.

Continuous efforts have been made for quality control of *D. officinale* based on qualitative and/or quantitative characterization, but the methods used are far from satisfactory. This herb has a unique chemical profile, in which carbohydrates account for up to 70%, along with some small molecules, such as bibenzyls and phenanthrenes, etc. Quality evaluation focusing on small molecules failed to efficiently distinguish *D. officinale* from other *Dendrobium* species. And in these studies, the investigated constituents were less than 0.21% of the whole herb material. In other words, more than 99% components in these samples were uncontrollable by these methods. On the other hand, with dominant content and proved bioactivities, carbohydrates are naturally the target in quality control of *D. officinale*. Nevertheless, as mentioned above, quality control of carbohydrates in *D. officinale*, just like other saccharide-dominant herbal materials, is also confronted with methodological bottleneck.

In Chinese Patent No. CN102370891A an approach focuses on small molecules and uses GPC column and UV detector, which is a complex and complicated approach not suitable for quick, efficient and low-cost application, is disclosed. The disclosed invention is hard to scale for commercial scale processing. While in another Chinese Patent No. CN101716283A and the publication in Journal of Pharmaceutical and Biomedical Analysis entitled *Comparison of polysaccharides from different Dendrobium using saccharide mapping* by J. Xu et. al, both disclosures are targeted on large molecule polysaccharides, which are also the target molecules of the present invention. However, the chemical markers they used are not the original *Dendrobium* polysaccharides, but the products of enzyme hydrolysis of the original *Dendrobium* polysaccharides. These documents disclosed a fingerprint of oligosaccharides produced by enzyme hydrolysis of *Dendrobium* polysaccharides, which would require complicated and time-consuming protocols, including water extraction, ethanol precipitation, deproteination, enzyme hydrolysis, and electrophoresis or HPLC.

Thus, there still exists a need for a quality control and authentication method of *D. officinale* that: 1) is rapid and low-cost; 2) with a mechanism that is easy-to-understand; 3) is simple; 4) is repeatable and reproducible in a satisfactory manner; 5) is practicable for both qualitative and quantitative analysis; 6) is reliable with large number of sample batches, and 7) is practical for commercial application.

Citation or identification of any reference in this section or any other sections of this application shall not be construed as an admission that such reference is available as prior art for the present application.

SUMMARY OF THE INVENTION

In accordance with a first aspect of the present invention, there is provided a method for authenticating a sample of carbohydrates-containing herbal material, comprising providing a chemical fingerprint of the carbohydrates in the sample based on molecular weight distribution; identifying one or more dominant polysaccharide components of the carbohydrates in the sample; separating the one or more dominant polysaccharide components; and developing a chemical marker to authenticate the herbal material.

In an embodiment of the first aspect, the step of providing the chemical fingerprint is conducted by means comprising a size exclusion chromatography.

In an embodiment of the first aspect, the size exclusion chromatography is a high performance gel permeation chromatography.

In an embodiment of the first aspect, the sample is extracted by a solvent prior to the step of providing the chemical fingerprint.

In an embodiment of the first aspect, the step of separating is conducted by means comprising filtration or precipitation.

In an embodiment of the first aspect, the filtration is an ultra centrifugal filtration.

In an embodiment of the first aspect, the precipitation is conducted by using 10-90% v/v ethanol.

In an embodiment of the first aspect, the step of developing the chemical marker is conducted by analyzing the one or more dominant polysaccharide components after the separating step by a high performance gel permeation chromatography.

In an embodiment of the first aspect, said herbal material comprises *Dendrobium* species.

In an embodiment of the first aspect, said *Dendrobium* species comprises *Dendrobium officinale*.

In accordance with a second aspect of the present invention, there is provided a method of preparing a chemical marker for use in qualitative and quantitative authentication of a sample of a carbohydrates-containing herbal material, comprising providing a chemical fingerprint of the carbohydrates in the sample based on molecular weight distribution; identifying one or more dominant polysaccharide components of the carbohydrates in the sample; separating the one or more dominant polysaccharide components to form one or more separated dominant polysaccharide components; and analysing the separated dominant polysaccharide components.

In an embodiment of the second aspect, the step of providing the chemical fingerprint is conducted by means comprising a size exclusion chromatography.

In an embodiment of the second aspect, the size exclusion chromatography is a high performance gel permeation chromatography.

In an embodiment of the second aspect, the sample is extracted by a solvent prior to the step of providing the chemical fingerprint.

In an embodiment of the second aspect, the step of separating is conducted by means comprising filtration or precipitation.

In an embodiment of the second aspect, the filtration is an ultra centrifugal filtration.

In an embodiment of the second aspect, the precipitation is conducted by using 10-90% v/v ethanol.

In an embodiment of the second aspect, said herbal material comprises *Dendrobium* species.

In an embodiment of the second aspect, said *Dendrobium* species comprises *Dendrobium officinale*.

BRIEF DESCRIPTION OF THE DRAWINGS

The above and other objects and features of the present invention will become apparent from the following description of the invention, when taken in conjunction with the accompanying drawings, in which.

DETAILED DESCRIPTION OF THE PREFERRED EMBODIMENTS

High performance gel permeation chromatography (HPGPC), a type of size exclusion chromatography that separates analytes on the basis of molecular size, is designed for analytical and preparative separation of synthesized water-soluble polymers, oligomers and biological substances such as polysaccharides, nucleic acids, proteins, peptides, etc. In the research on herbal materials, HPGPC is widely employed for homogeneity and molecular weight determination of purified polysaccharides or oligosaccharides by qualitatively characterizing peak symmetry and calculating with established retention time-molecular weight standard curve, respectively. To the best of our knowledge, however, it has never been used for either quality control or for quantitative determination of carbohydrates in herbal materials.

Figure 1:
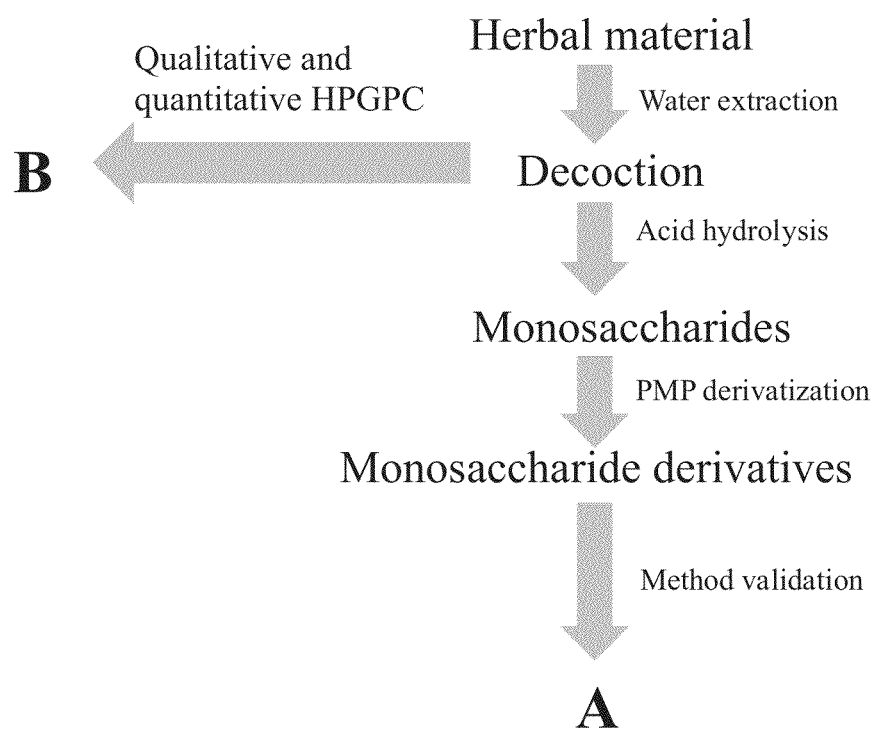
FIG. 1 is a flow chart showing a conventional sugar composition analysis (A); and the High Performance Gel Permeation Chromatography (HPGPC) based method (B) in accordance with the present invention, for quality control of carbohydrates in herbal materials.

In an embodiment of the present invention, taking *D. officinale* as a model herb, a novel and rapid HPGPC based method was developed for quality control of carbohydrates in herbal materials. Firstly, a compartmental HPGPC fingerprint based on molecular weight distribution of carbohydrate components was established for qualitative identification of *D. officinale*. Subsequently, the dominant polysaccharide peak in the GPC chromatogram was separated and then regarded as an unique holistic chemical marker for quality evaluation of the carbohydrates in *D. officinale* by quantitative determination, see route B of FIG. 1. Besides, the conventional method, sugar composition analysis, as shown in route A of FIG. 1, was also performed and compared, and the results are shown in Table 1.

EXPERIMENTAL

Materials and Chemicals

The commercial *Tiepi Fengdou* samples were purchased from different locations in China. The authentic *Tiepi Fengdou* samples, and other *Dendrobium* species samples, namely

Figure 2:
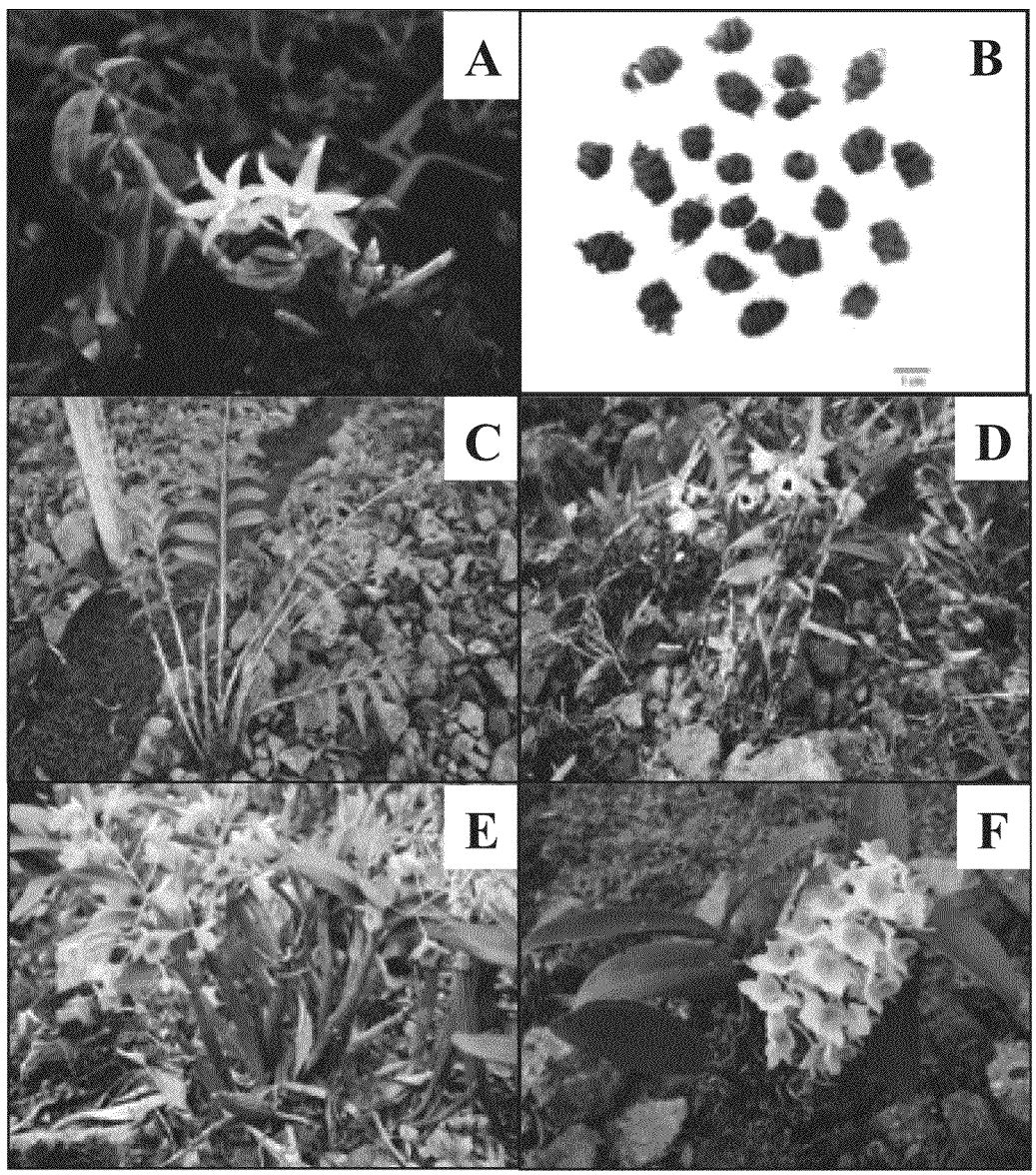
FIG. 2 shows photographs of the original plants of *Dendrobium officinale* [*D. officinale*] (A), *Dendrobium fimbriatum* [*D. fimbriatum*] (C), *Dendrobium nobile* [*D. nobile*] (D), *Dendrobium chrysotoxum* [*D. chrysotoxum*] (E), *Dendrobium thyrsiflorum* [*D. thyrsiflorum*] (F) and *Tiepi Fengdou* (B) which is the commercial product of *D. officinale*.

*D. fimbriatum, D. nobile, D. chrysotoxum* and *D. thyrsiflorum* as shown in FIG. 2, were provided by several certificated producing areas in mainland China and were authenticated by both the conventional sugar composition analysis and the HPGPC quantitative analysis, with the results being shown in Table 1. The voucher specimens were deposited at School of Chinese Medicine, Hong Kong Baptist University, Hong Kong.

Water Extraction:

Dried sample powder (0.10 g) was extracted with water at 100° C. (5 mL×1 h×2 times). The extracted solutions were centrifuged at 3500 rpm for 10 min and the supernatants were then combined for further analysis.

HPGPC Conditions:

The prepared water extracts of *Dendrobium* samples were directly analyzed using HPGPC performed on an Agilent

TABLE 1

Quantitative results of carbohydrate components in the investigated Tiepi Fengdou samples and the *Dendrobium* species samples (mg/g) based on sugar composition analysis and HPGPC analysis

| | | | Sugar composition analysis | | | | | | HPGPC quantitative analysis |
|---|---|---|---|---|---|---|---|---|---|
| | | | Water extracts | | | Peak I | | | |
| Sample code | Sample name | Locality | D-mannose | D-glucose | Total | D-mannose | D-glucose | Total | Peak I |
| | | | Authentic Tiepi Fengdou samples | | | | | | |
| ATF-01 | Tiepi Fengdou | Yunnan, China | 419.40[a] | 62.51 | 481.90 | 250.70 | 41.98 | 292.68 | 300.62 |
| ATF-02 | | Guangxi, China | 385.64 | 73.46 | 459.10 | 269.72 | 42.21 | 311.93 | 310.37 |
| ATF-03 | | Yunnan, China | 416.55 | 61.98 | 478.53 | 250.83 | 36.00 | 286.83 | 306.95 |
| ATF-04 | | Yunnan, China | 388.57 | 74.53 | 463.09 | 246.12 | 43.30 | 289.42 | 324.40 |
| ATF-05 | | Zhejiang, China | 437.57 | 63.42 | 500.99 | 261.57 | 46.75 | 308.32 | 323.31 |
| ATF-06 | | Zhejiang, China | 393.52 | 66.64 | 460.16 | 277.54 | 55.96 | 333.50 | 307.29 |
| ATF-07 | | Anhui, China | 387.01 | 76.34 | 463.34 | 272.30 | 51.29 | 323.58 | 326.43 |
| ATF-08 | | Guangxi, China | 444.09 | 62.02 | 506.11 | 279.87 | 50.36 | 330.23 | 318.57 |
| ATF-09 | | Guangxi, China | 435.31 | 68.07 | 503.38 | 252.00 | 39.75 | 291.76 | 329.04 |
| ATF-10 | | Zhejiang, China | 435.91 | 72.96 | 508.87 | 243.38 | 35.98 | 279.36 | 304.08 |
| | | | Commercial Tiepi Fengdou samples | | | | | | |
| CTF-01 | Tiepi Fengdou | Hong Kong | 412.31 | 73.50 | 485.81 | 306.28 | 36.42 | 342.70 | 365.24 |
| CTF-02 | | Hong Kong | 328.73 | 68.58 | 397.31 | 248.18 | 24.74 | 272.92 | 297.90 |
| CTF-03 | | Hong Kong | 465.79 | 72.90 | 538.70 | 291.13 | 45.64 | 336.77 | 314.20 |
| CTF-04 | | Guangzhou, China | 395.46 | 57.23 | 452.70 | 193.06 | 8.58 | 201.63 | 237.08 |
| CTF-05 | | Guangzhou, China | 440.82 | 115.75 | 556.57 | 314.19 | 46.94 | 361.13 | 329.57 |
| CTF-06 | | Hong Kong | 316.35 | 122.68 | 439.03 | 176.46 | 56.54 | 232.99 | 222.21 |
| CTF-07 | | Hong Kong | 267.31 | 119.51 | 386.82 | 112.63 | 60.28 | 172.90 | 150.44 |
| CTF-08 | | Hong Kong | 178.30 | 84.97 | 263.27 | 139.58 | 59.24 | 198.82 | 201.43 |
| CTF-09 | | Anhui, China | 274.87 | 113.92 | 388.78 | 221.37 | 52.91 | 274.28 | 266.59 |
| CTF-10 | | Hong Kong | 302.39 | 93.82 | 396.22 | 286.70 | 22.85 | 309.56 | 331.49 |
| CTF-11 | | Hong Kong | 182.55 | 94.59 | 277.14 | 87.90 | 1.44 | 89.34 | 100.12 |
| CTF-12 | | Jiangsu, China | 195.69 | 165.29 | 360.98 | 162.14 | 40.04 | 202.18 | 196.92 |
| CTF-13 | | Anhui, China | 378.04 | 95.95 | 473.99 | 237.77 | 57.76 | 295.53 | 291.81 |
| | | | Other *Dendrobium* species | | | | | | |
| DF | *D. fimbriatum* | Yunnan, China | 122.02 | 59.99 | 182.01 | 27.33 | 8.02 | 35.35 | 44.81 |
| DN | *D. nobile* | Yunnan, China | 44.94 | 38.66 | 83.60 | 13.57 | 6.47 | 20.04 | —[b] |
| DC | *D. chrysotoxum* | Yunnan, China | 131.88 | 181.13 | 313.01 | 130.44 | 76.87 | 207.31 | 215.91 |
| DT | *D. thyrsiflorum* | Yunnan, China | 187.44 | 76.15 | 263.58 | 28.14 | 13.04 | 41.17 | 35.16 |

[a]The data was present as average of duplicates;
[b]Under the limit of quantification HPGCP Quantitative Analysis Acetonitrile and ammonium acetate for High Performance Liquid Chromatography (HPLC) analysis were purchased from Merck (Darmstadt, Germany). Deionized water was prepared by Millipore Milli Q-Plus system (Millipore, Bedford, Mass., USA). Trifluoroacetic acid (TFA) used for acid hydrolysis of carbohydrates was from Riedel-de Haën (Honeywell International Inc., Germany). 1-Phenyl-3-methyl-5-pyrazolone (PMP) for monosaccharide derivatization was bought from Sigma (St. Louis, Mo., USA). The reference substances, D-galacturonic acid monohydrate (GalA), D-glucuronic acid (GlcA), L-arabinose (Ara), D-mannose (Man), D-galactose (Gal), D-glucose (Glc), L-rhamnose monohydrate (Rha), D-fucose (Fuc) and D-ribose (Rib), and a series of Dextrans with different molecular weights (1 kDa; 5 kDa; 12 kDa; 25 kDa; 50 kDa; 80 kDa; 150 kDa; 270 kDa; 410 kDa and 670 kDa) were purchased from Sigma (St. Louis, Mo., USA).

1100 series HPLC-DAD system (Agilent Technologies, Palo Alto, Calif.) coupled with evaporative light scattering detector (ELSD). The separation was achieved on a two tandem TSK GMPWXL columns (300 mm×7.8 mm i.d., 10 µm) system operated on 40° C. Ammonium acetate aqueous solution (20 mM) was used as mobile phase at a flow rate of 0.6 mL/min. The signal from ELSD was transmitted to Agilent Chemstation for processing through an Agilent 35900E interface. The parameters of ELSD were set as follows: the drift tube temperature was 120° C. and nebulizer nitrogen gas flow rate was at 3.2 L/min, impact off mode. An aliquot of 20 µL solution was injected for analysis. UV detection wavelength was set at 260 and 280 nm.

Aqueous stock solutions of dextrans (2 mg/mL) with different molecular weights (1 kDa; 5 kDa; 12 kDa; 25 kDa; 50 kDa; 80 kDa; 150 kDa; 270 kDa; 410 kDa and 670 kDa) and glucose were, respectively, injected to HPGPC using the same conditions for the construction of molecular weight-retention time calibration curve by plotting logarithm of the peak area versus the retention time of each analyte.

HPGPC-Guided Chemical Marker Separation:

The dominant peak in the HPGPC fingerprints of *Tiepi Fengdou*, which is the most of the polysaccharides in *Tiepi Fengdou*, were separated and obtained using ultra centrifugal filters or precipitation with ethanol (10-90% v/v) [molecular weight cut-off (MWCO)=10 kDa, wherein molecules with molecular weight of at least 10 kDa and higher are separated and obtained] (Millipore, Billerica, Mass.). In detail, the water extract of *D. officinale* (15 mL) were transferred into the ultra-centrifugal filter tube and then centrifuged at 4000×g in eight times (15 min each). Finally, the remains were re-dissolved in 15 mL water and then freeze dried for further analysis. The precipitation was operated as follows: firstly, ethanol (>90% v/v) was added into the water extract and fully mixed to make the ethanol concentration reach 10-90% v/v; then, stayed overnight and combined the precipitate; finally freeze dried for further analysis.

HPGPC Quantitative Method Validation:

The HPGPC method for quantitative analysis of the separated holistic polysaccharide marker (the dominant peak in GPC chromatograms) was validated in terms of linearity, sensitivity, precision, accuracy and stability.

Aqueous stock solution of the chemical marker was diluted to appropriate concentrations for the construction of calibration curve. Six concentrations of the solution were analyzed in triplicates, and the calibration curves were constructed by plotting logarithm of the peak areas versus logarithm of the concentrations of the marker.

The stock solutions were diluted to a series of appropriate concentrations with aqueous solutions, and an aliquot of the diluted solutions were injected into HPLC for analysis. The limits of detection (LODs) and limits of quantification (LOQs) under the present conditions were determined at an S/N (signal to noise) of about 3 and 10, respectively.

Intra- and inter-day variations were chosen to determine the precision of the developed assay. For intra-day variability test, the *Tiepi Fengdou* sample ATF-03 (as shown in Table 1) was extracted and analyzed for six replicates within one day, while for inter-day variability test; the same sample was examined in duplicates for consecutive three days. Variations for logarithm of the peak areas were expressed by the RSDs of the data.

The spike recovery test was used to evaluate the accuracy of the method. About 0.05 g of *Dendrobium* sample (ATF-03) with known contents of the target chemical marker was weighed, and different amounts (high, middle and low level) of the marker were spiked, then extracted and analyzed in triplicates. The spike recoveries were calculated by following equation:

Spike recovery (%)=(total amount detected−amount original)/amount spiked×100%.

The stability test was performed by analyzing the sample ATF-03 extract over period of 2 h, 4 h, 6 h, 8 h, 12 h, 24 h, the RSD for the logarithm of the marker peak areas was taken as the measures of stability.

Sugar Composition Analysis

Acid Hydrolysis of Water Extracts:

The prepared water extracts solution (0.50 mL) was mixed with 2.50 mL of trifluoroacetic acid (TFA) (final concentration 2 M) solution in a screw-cap vial, and hydrolyzed for 2 h at 120° C. After cooling, the hydrolysate was evaporated at 55° C. on a rotary evaporator until dry. Then 1 mL aqueous solution was added to dissolve the hydrolysate, and the precipitate was removed after centrifugation (15700×g, 5 min), the supernatant was then subjected to 1-phenyl-3-methyl-5-pyrazolone (PMP) derivatization.

PMP Derivatization of Monosaccharides:

The sugar derivatization was performed according to publication in Journal of Pharmaceutical and Biomedical Analysis entitled *Comparison of polysaccharides from different Dendrobium using saccharide mapping* by J. Xu et. al with modifications. Briefly, the acid hydrolysate (100 μL) was mixed with the same volume of ammonia water and 0.5 M PMP methanolic solution (200 μL). The mixture was allowed to react at 70° C. for 30 min and then was cooled to room temperature. Afterwards, 100 μL glacial acetic acid and 500 μL chloroform were successively added in to neutralize the reaction solution and remove the excess PMP reagents, respectively. After vigorous shaking followed by centrifugation at 15700×g for 5 min, organic phase was discarded. The operation was performed five times, and finally the aqueous layer was diluted 10 times and filtered through a 0.22 μm syringe filter (Agilent Technologies, USA) before Liquid Chromatography With Diode Array Detection (LC-DAD) analysis. A standard solution, containing 7 monosaccharides (Rha, Ara, Fuc, Man, Glu, Gal and Rib) and 2 uronic acids (GlcA and GalA), was also treated as mentioned above.

HPLC Analysis:

Analysis of PMP derivatives of released monosaccharides in *Dendrobium* aqueous extracts after acid hydrolysis was performed on an Agilent 1100 series HPLC-DAD system (Agilent Technologies, Palo Alto, Calif.) which was equipped with a vacuum degasser, a binary pump, an autosampler and a diode array detector. Samples (5 μL) were injected onto Grace Alltima™ C18 column-W (250 mm×4.6 mm i.d., 5 μm) operated at 30° C. The separation was achieved using gradient elution with 100 mM ammonium acetate aqueous solution (A) (pH=5.58) and acetonitrile (B) at a flow rate of 1.0 mL/min: 0~5 min, 17~20% B; 5~30 min, 20~28% B; 30-35 min, 28% B. UV detection wavelength was set at 245 nm.

The HPLC method for quantitative analysis of the compositional monosaccharides was also validated with regard to linearity, sensitivity, precision, accuracy and stability.

Data Analysis:

To evaluate the quality consistency of the investigated *Dendrobium* samples, a three-dimensional graphics of principal component analysis (3D-PCA) was performed by Simca-P+ 9 (Umetrics, AN MKS company, Sweden), which comprise a number of "procedures" i.e. graphical, statistical, reporting, processing and tabulating procedures—that enable simple and rapid data evaluation.

Results and Discussion

Sugar Composition Analysis:

The compositional monosaccharides in the water extracts of investigated *Dendrobium* samples were determined using the established HPLC method. The typical chromatograms and calculated contents of the released monosaccharides after acid hydrolysis in water extracts of all *Dendrobium* samples were summarized in FIG. 5 and Table 1, respectively. The analysis demonstrated that sugar composition exhibited highly qualitative consistence in all *Dendrobium* samples. There were mainly two compositional monosaccharides, Man and Glc, in the water extracts of the *Dendrobium* samples. In addition, the quantitative results of the two compositional monosaccharides in some of the samples were also similar. It has been clearly proved that sugar composition analysis was poor in selectivity and therefore might hinder the authentication and quality evaluation of *D. officinale*. Besides, the experimental procedure was so complicated that the quantitative results could be influenced by multiple factors.

HPGPC Qualitative Analysis:

Total *Dendrobium* samples were qualitatively analyzed by HPGPC. Firstly, water extracts of ten batches of authentic *Tiepi Fengdou* samples (as shown in Table 1) were analyzed and compared using HPGPC-DAD-ELSD, in which UV 260 nm and 280 nm were selected for monitoring saccharide-conjugated nucleic acid and/or peptide, and the major peaks had no obvious absorbance under the investigated conditions (data not shown). The GPC chromatograms of the 10 batches of *Tiepi Fengdou* samples were shown in FIG. 3A and, surprisingly, the results presented extremely similar chromatographic characteristics. According to the GPC chromatograms, three peaks, namely peak I (MW>15.92 kDa), peak II (MW: 0.65-15.92 kDa), and peak III (MW<0.65 kDa), as calculated by the established molecular weight-retention time calibration curve, could be found in these *Tiepi Fengdou* samples based on their molecular distribution and peak I was found to be the majority. The results could preliminarily demonstrate the quality of the ten batches of authentic *Tiepi Fengdou* samples are presented consistently and the chromatograms could be regarded as the HPGPC fingerprints for qualitative identification of *Tiepi Fengdou*.

Figure 3:
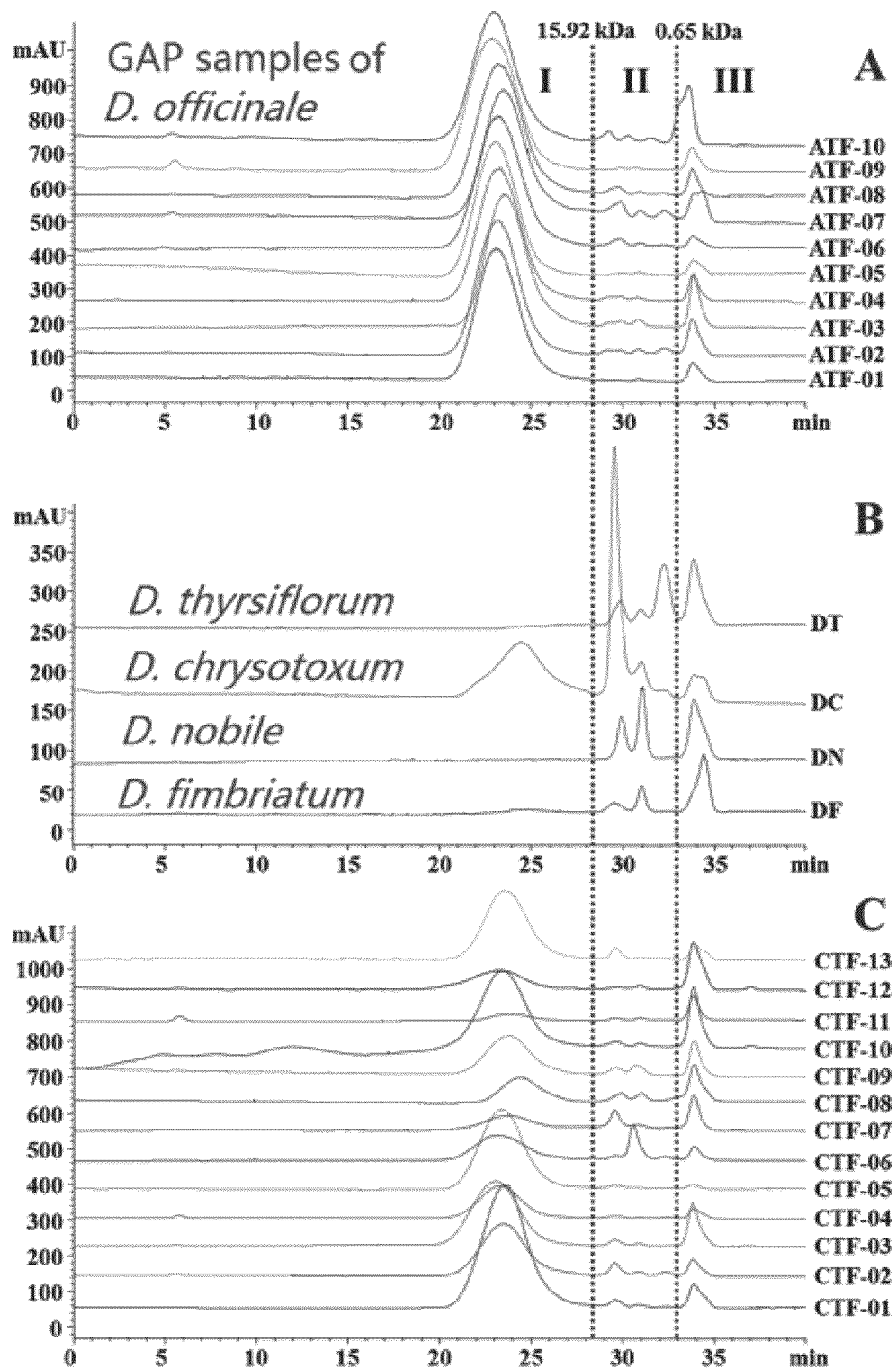
FIG. 3 shows the HPGPC chromatograms of water extracts from authentic *Tiepi Fengdou* samples (A), other *Dendrobium* species (B) and commercial *Tiepi Fengdou* samples (C).

Then, four other commonly used *Dendrobium* species samples, including *D. nobile, D. thyrsiflorum, D. fimbriatum* and *D. chrysotoxum* were also analyzed and the results showed that their GPC chromatograms are apparently different from that of *D. officinale* with regard to not only molecular size range but also the peak pattern (FIG. 3B). Among them peak I was hardly detectable in most of these samples, for example, *D. nobile*, which is one of the most frequently used substitutes of *D. officinale*. The results clearly stated that carbohydrates in *D. officinale* are characteristic and are dissimilar with those of the other similar species.

Finally, thirteen batches of commercial *Tiepi Fengdou* samples were investigated and their GPC chromatograms were summarized in FIG. 3C. It could be intuitively seen that they are similar with the chromatograms of the authentic samples and are distinctively different with those of the other *Dendrobium* species samples. However, based on the chromatograms, although the molecular weight ranges of carbohydrates in these commercial samples are similar with the authentic ones, the distributions were inconsistent. For example, in the chromatograms of some commercial samples, for example CTF-07, 11 and 12, peak I are sharply decreased while the peak III become dominant compared with those of authentic *Tiepi Fengdou* samples. The HPGPC analysis results could partly illustrate that all these commercial samples might be derived from *D. officinale* plants but their quality were not controlled well.

Figure 6:
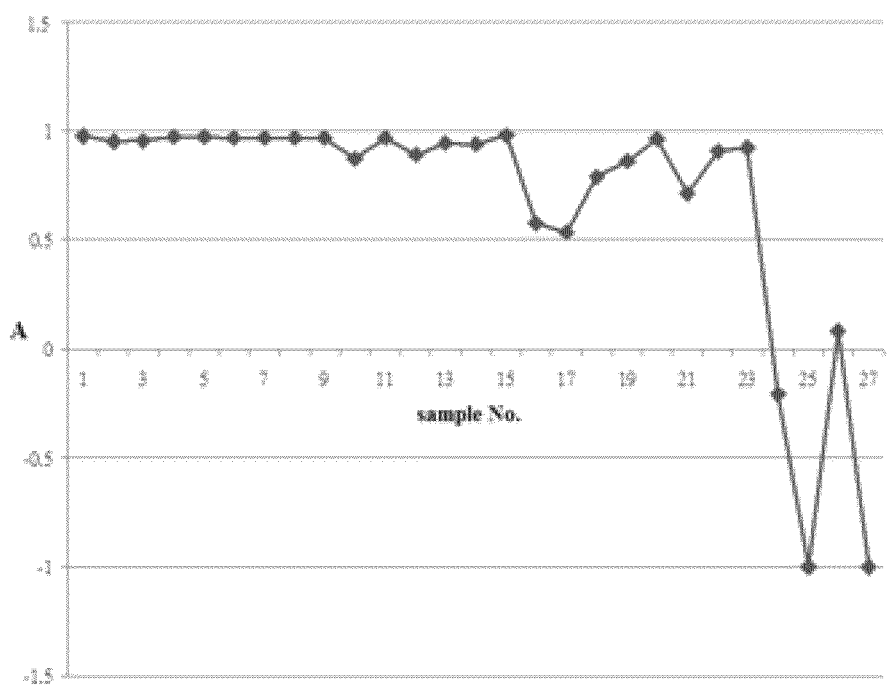
FIG. 6 shows authentication results of authentic and commercial *Tiepi Fengdou* samples and other *Dendrobium* species samples based on the fingerprint analysis.

The classification of *Dendrobium* samples was easily done using a HPGPC fingerprint parameter A=(PI−PII)/(PI+PII) in which PI is the peak area of peak I; PII is the peak area sum of peak II As shown in FIG. 6, sample whose A is above 0.3 is defined as *Tiepi Fengdou*, those with A as being smaller than or equal to 0.3 is defined as other *Dendrobium* species.

The above obtained results of HPGPC analysis should be more reasonable than those obtained from the sugar composition analysis. For example, as shown in Table 1, the carbohydrate components in CTF-08 and DT should be qualitatively and quantitatively consistent in view of their similar monosaccharide compositions based on the sugar composition analysis. However, in accordance with HPGPC chromatograms, the carbohydrate components of these samples are definitely different. It is known that sugar composition analysis is built on breakdown of original existential state of carbohydrates in herbal materials, in particular, polysaccharides and oligosaccharides. It can be easily understand that there are no necessary relationship between the compositional monosaccharides and the holistic chemical properties, such as molecular weight, of the carbohydrate components, which are very important for the carbohydrate-based quality control of herbal materials. It could therefore be concluded that the sugar composition analysis method seemed to be less reasonable and might provide confusing results on the quality control of *Tiepi Fengdou*. Conversely, the HPGPC fingerprint, which do not require any sample pretreatment and therefore is much more convenient than sugar the composition analysis, could intuitively provide the original characteristics of the carbohydrates in molecular weight distribution and is proved to be efficient for authentication and quality evaluation of *Tiepi Fengdou*.

Figure 4:
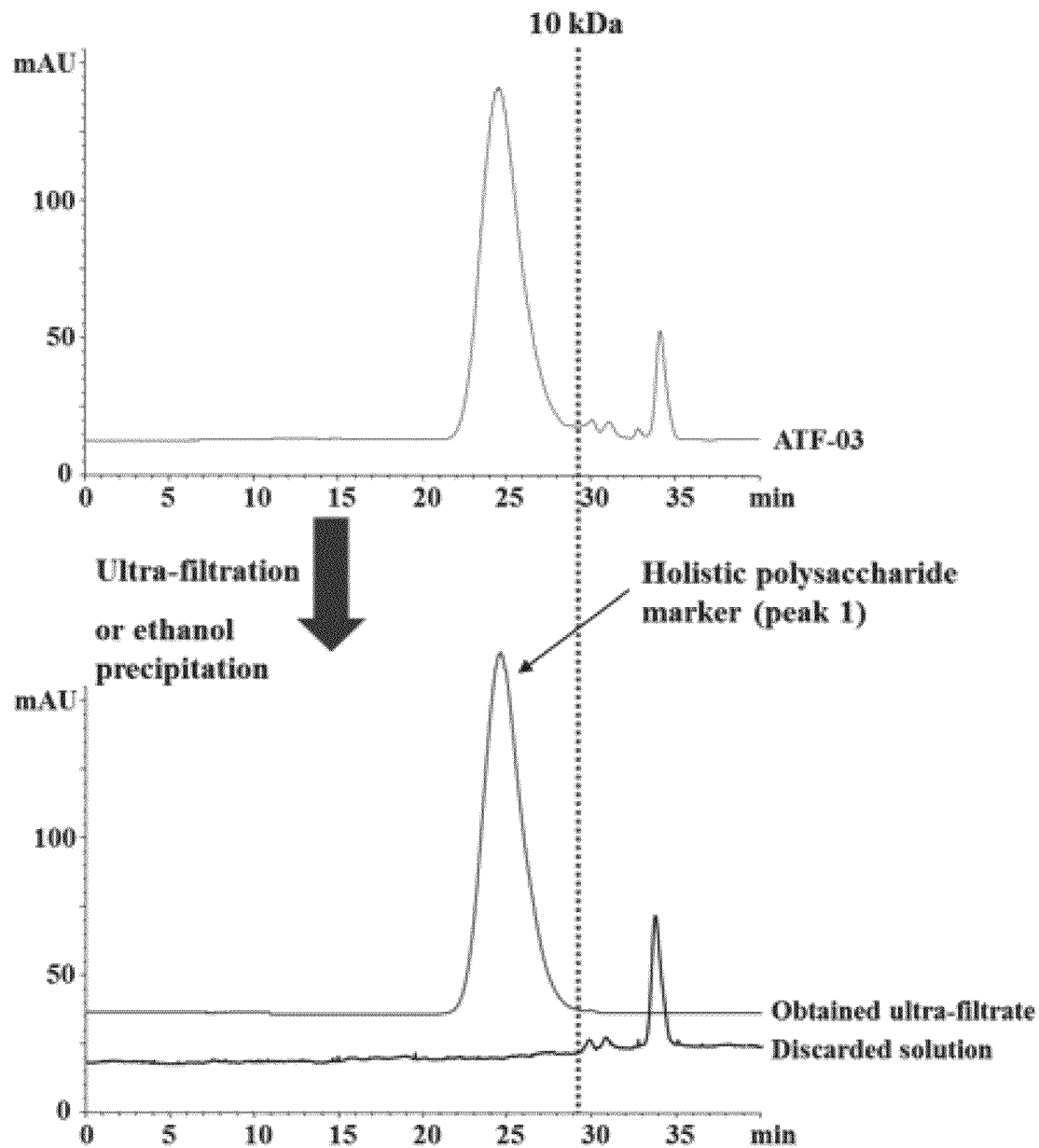
FIG. 4 shows preparation of the holistic polysaccharides marker (peak I).
Figure 5:
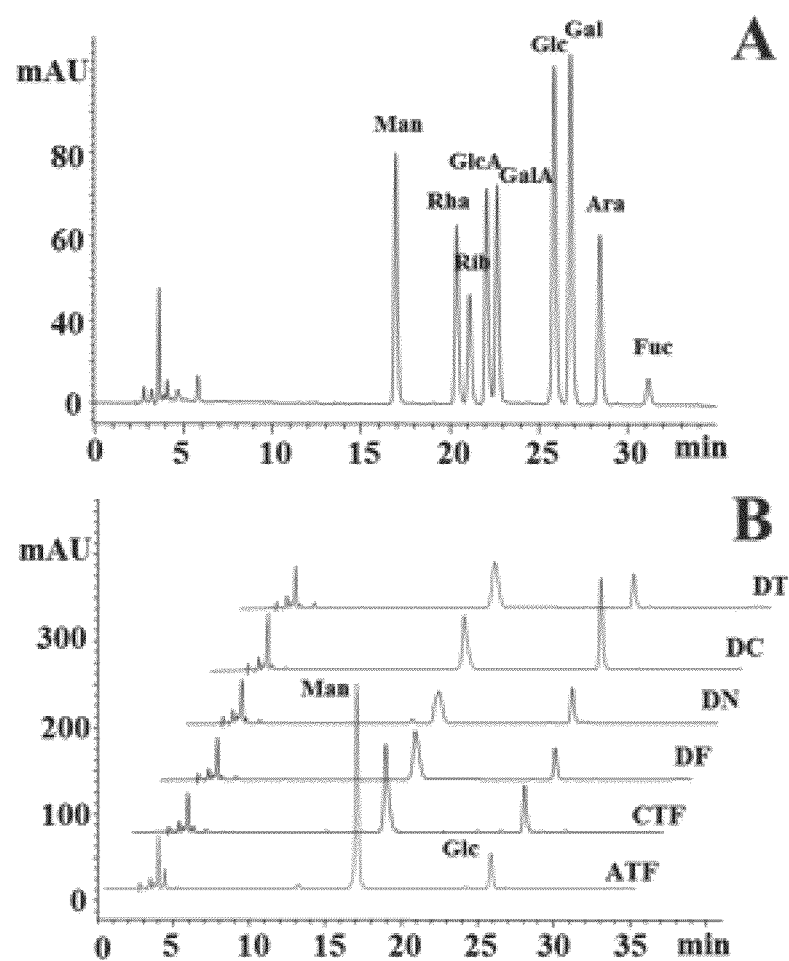
FIG. 5 shows the HPLC chromatograms of compositional monosaccharides analysis in mixed monosaccharide standards (A) and authentic and commercial *Tiepi Fengdou* samples and other *Dendrobium* species samples (B).
Figure 7:
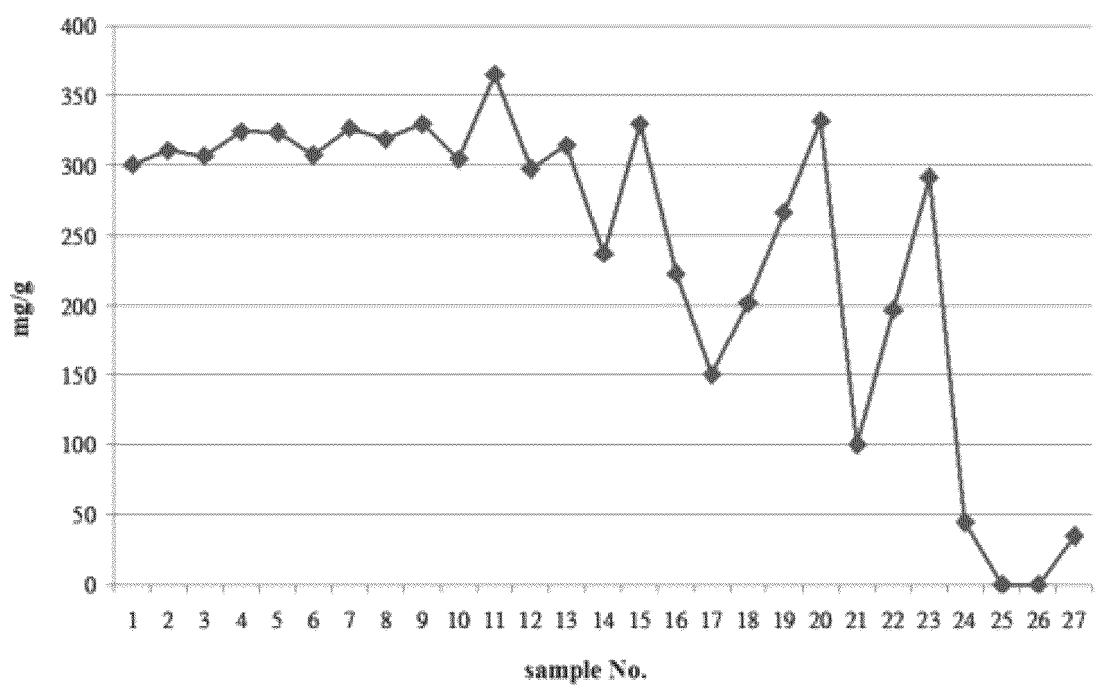
FIG. 7 shows the contents of the polysaccharide marker in tested *Dendrobium* samples by HPGPC quantitative analysis.

HPGPC Quantitative Analysis:

Except for qualitative identification, the highly consistent GPC chromatograms of ten batches of the authentic *Tiepi Fengdou* samples also inspired that the dominant polysaccharide peak (peak I), as the vast majority of carbohydrate components, could be separated and regarded as the unique chemical marker for quantitative quality control of *Tiepi Fengdou*. Thus, in this study, peak I of ten batches of the authentic *Tiepi Fengdou* samples was purified as shown in FIG. 4 and the qualitative consistency of the separated peaks were then further confirmed in terms of their highly similar compositional monosaccharides as shown in FIG. 5, with peak area ratios of Man and glc as being 5.37~6.17. After that, the obtained chemical marker was used for quantitative determination of all investigated *Dendrobium* samples, and the method was also validated just like conventional quantitative analysis of small molecules. The quantitative results were summarized in Table 1 and FIG. 7. It was illustrated that the contents of the chemical marker in ten batches of the authentic *Tiepi Fengdou* samples were closely around 300 mg/g while the other *Dendrobium* species samples were with contents of below 50 mg/g and even down to zero mg/g. The content varied in commercial samples. The quality of the *Tiepi Fengdou* decreases with decreasing contents of the chemical marker.

CONCLUSION

In the present invention, by taking *D. officinale* as a model herb, a novel and rapid HPGPC-based method was developed for quality control of saccharide-dominant herbal materials by simultaneously qualitative and quantitative characterization of carbohydrate components, in which HPGPC fingerprint and the holistic polysaccharide marker were firstly proposed and demonstrated, and HPGPC was also firstly employed for quantitative purpose. The experimental results indicated that the newly-established method was more efficient, stable and convenient with reduced uncertainties in qualitative and quantitative evaluation of *D. officinale* when compared to the currently available methods. Although *D. officinale* has been used as a model herb, it is understandable that the present invention should also be practicable for the quality control of other saccharide-dominant herbal materials and products.

In summary, the present invention relates to a quality control marker and method of using such marker in qualitative and quantitative authentication of herbal material, particularly *Dendrobium* sp. The present invention also relates to a chemical marker and its use in quick, efficient and low-cost authentication of *Dendrobium officinale* Kimura et Migo, which is well-known as an expensive Chinese medicine under the name of *Tiepi Shihu* (鉄皮石斛). In the present invention, the chemical marker that based on *Dendrobium officinale* could be easily distinguished from other *Dendrobium* species in a rapid and economic way. This invention could be widely applied for authentication of *Dendrobium officinale* by testing laboratories, pharmaceutical factories, and research institutions.

If desired, the different functions discussed herein may be performed in a different order and/or concurrently with each other. Furthermore, if desired, one or more of the above-described functions may be optional or may be combined.

While the foregoing invention has been described with respect to various embodiments and examples, it is understood that other embodiments are within the scope of the present invention as expressed in the following claims and their equivalents. Moreover, the above specific examples are to be construed as merely illustrative, and not limitative of the remainder of the disclosure in any way whatsoever. Without further elaboration, it is believed that one skilled in the art can, based on the description herein, utilize the present invention to its fullest extent. All publications recited herein are hereby incorporated by reference in their entirety.

Those skilled in the art will appreciate that the invention described herein is susceptible to variations and modifications other than those specifically described.

The invention includes all such variations and modifications. The invention also includes all of the steps and features referred to or indicated in the specification, individually or collectively and any and all combinations or any two or more of the steps or features.

Throughout this specification, unless the context requires otherwise, the word "comprise" or variations such as "comprises" or "comprising", will be understood to imply the inclusion of a stated integer or group of integers but not the exclusion of any other integer or group of integers. It is also noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

Furthermore, throughout the specification and claims, unless the context requires otherwise, the word "include" or variations such as "includes" or "including", will be understood to imply the inclusion of a stated integer or group of integers but not the exclusion of any other integer or group of integers.

Other definitions for selected terms used herein may be found within the detailed description of the invention and apply throughout. Unless otherwise defined, all other technical terms used herein have the same meaning as commonly understood to one of ordinary skill in the art to which the invention belongs.

Other aspects and advantages of the invention will be apparent to those skilled in the art from a review of the ensuing description.

The invention claimed is:

1. A method for authenticating a sample of herbal material from the *Dendrobium* species, comprising:
   a. providing a chemical fingerprint of the carbohydrates in the sample based on molecular weight distribution;
   b. identifying one or more dominant polysaccharide components of the carbohydrates in the sample, the sample having an amount of polysaccharides, where the one or more dominant polysaccharide components are the one or more components of the sample having the most of said amount of polysaccharides in said sample;
   c. separating the one or more dominant polysaccharide components; and
   d. authenticating said sample of herbal material using the separated one or more dominant polysaccharide components.

2. The method according to claim 1, wherein the step of providing the chemical fingerprint includes performing size exclusion chromatography.

3. The method according to claim 2, wherein the size exclusion chromatography is a high performance gel permeation chromatography.

4. The method according to claim 3, wherein authenticating said sample of herbal material using the separated one or more dominant polysaccharide components is conducted by analyzing the one or more dominant polysaccharide components after the step of providing a chemical fingerprint by a high performance gel permeation chromatography.

5. The method according to claim 1, wherein the sample is extracted by a solvent prior to the step of providing the chemical fingerprint.

6. The method according to claim 1, wherein the step of separating is selected from the group consisting of filtration and precipitation.

7. The method according to claim 6, wherein the step of separating includes filtration and the filtration is an ultra centrifugal filtration.

8. The method according to claim 6, wherein the step of separating includes precipitation and the precipitation is conducted by using 10-90% v/v ethanol.

9. The method according to claim 1, wherein said *Dendrobium* species comprises *Dendrobium officinale*.

10. A method of preparing a chemical marker for use in qualitative and quantitative authentication of a sample of a herbal material from the *Dendrobium* species, comprising:
    a. providing a chemical fingerprint of the carbohydrates in the sample based on molecular weight distribution;
    b. identifying one or more dominant polysaccharide components of the carbohydrates in the sample, the sample having an amount of polysaccharides, where the one or more dominant polysaccharide components are the one or more components of the sample having the most of said amount of polysaccharides in said sample;
    c. separating the one or more dominant polysaccharide components to form one or more separated dominant polysaccharide components; and
    d. analysing the separated dominant polysaccharide components as the chemical marker for use in qualitative and quantitative authentication of said sample.

11. The method according to claim 10, wherein the step of providing the chemical fingerprint includes performing is conducted by means comprising a size exclusion chromatography.

12. The method according to claim 11, wherein the size exclusion chromatography is a high performance gel permeation chromatography.

13. The method according to claim 10, wherein the sample is extracted by a solvent prior to the step of providing the chemical fingerprint.

14. The method according to claim 10, wherein the step of separating is selected from the group consisting of filtration and precipitation.

15. The method according to claim 14, wherein the step of separating includes filtration and the filtration is an ultra centrifugal filtration.

16. The method according to claim 14, wherein the step of separating includes precipitation and the precipitation is conducted by using 10-90% v/v ethanol.

17. The method according to claim 10, wherein said *Dendrobium* species comprises *Dendrobium officinale*.

* * * * *